United States Patent
Grammenos et al.

(10) Patent No.: US 6,187,816 B1
(45) Date of Patent: Feb. 13, 2001

(54) PHENYLKETIMINOOXYBENZYL COMPOUNDS, METHOD FOR THE PRODUCTION AND USE THEREOF

(75) Inventors: Wassilios Grammenos, Ludwigshafen; Hubert Sauter; Herbert Bayer, both of Mannheim; Thomas Grote, Schifferstadt; Andreas Gypser, Mannheim; Reinhard Kirstgen, Neustadt; Bernd Müller, Frankenthal; Arne Ptock, Ludwigshafen; Franz Röhl, Schifferstadt; Roland Götz, Rothenburg; Gisela Lorenz, Neustadt; Eberhard Ammermann, Heppenheim; Siegfried Strathmann, Limburgerhof; Volker Harries, Frankenthal, all of (DE)

(73) Assignee: BASF Aktiengesellschaft, Ludwigshafen (DE)

( * ) Notice: Under 35 U.S.C. 154(b), the term of this patent shall be extended for 0 days.

(21) Appl. No.: 09/381,048

(22) PCT Filed: Mar. 6, 1998

(86) PCT No.: PCT/EP98/01323
§ 371 Date: Sep. 14, 1999
§ 102(e) Date: Sep. 14, 1999

(87) PCT Pub. No.: WO98/41498
PCT Pub. Date: Sep. 24, 1998

(30) Foreign Application Priority Data

Mar. 18, 1997 (DE) .............................. 197 11 168

(51) Int. Cl.$^7$ ................................ A01N 37/00
(52) U.S. Cl. ..................... 514/539; 514/538; 560/35; 564/256
(58) Field of Search ................ 560/35; 564/164, 564/253, 256, 257, 259, 265; 514/532, 534, 535, 538, 539, 619, 622, 640

(56) References Cited

U.S. PATENT DOCUMENTS

| 4,957,937 | 9/1990 | Schuetz et al. | 514/407 |
| 5,194,662 | 3/1993 | Brand et al. | 560/35 |
| 5,985,921 | * 11/1999 | Farooq et al. | 514/538 |
| 5,994,359 | * 11/1999 | Grote | 514/255 |

FOREIGN PATENT DOCUMENTS

| 2043733 | 12/1991 | (CA) . |
| 472300 | 2/1992 | (EP) . |
| 92/13830 | * 8/1992 | (WO) . |

OTHER PUBLICATIONS

CA:122:9686 abs of EP 585751, Apr. 1994.*
CA:116:151325 abs of EP463488, Jan. 1992.*
CA:116:255331 abs of EP460575, Dec. 1991.*

* cited by examiner

Primary Examiner—Jean F Vollano
(74) Attorney, Agent, or Firm—Keil & Weinkauf

(57) ABSTRACT

Phenylketiminooxybenzyl compounds of the general formula I

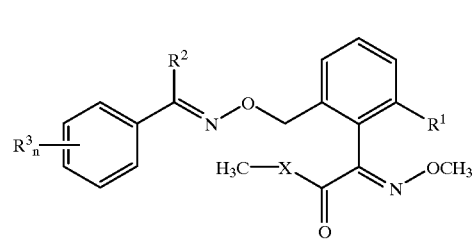

(I)

where:
X is O or NH;
$R^1$ is fluorine, chlorine, alkyl, haloalkyl, alkoxy and haloalkoxy;
$R^2$ is halogen, alkyl, haloalkyl and alkoxy;
$R^3$ is halogen, alkyl, haloalkyl, alkoxy, haloalkoxy, cycloalkyl, unsubstituted or substituted phenyl, unsubstituted or substituted phenoxy or $CR^a$=$NOR^b$ ($R^a$= hydrogen or alkyl; $R^b$=alkyl, alkenyl or alkynyl);
n is 1, 2 or 3,
and salts thereof, processes for their preparation and their use for controlling animal pests and harmful fungi.

18 Claims, No Drawings

PHENYLKETIMINOOXYBENZYL COMPOUNDS, METHOD FOR THE PRODUCTION AND USE THEREOF

The present invention relates to phenylketiminooxybenzyl compounds of the general formula I

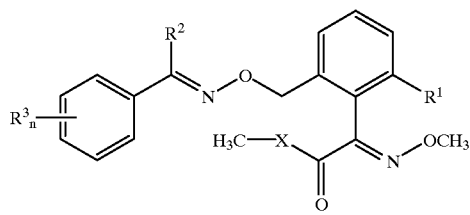

(I)

where:
- X is O or NH;
- $R^1$ is fluorine, chlorine, $C_1$–$C_4$-alkyl, $C_1$–$C_4$-haloalkyl, $C_1$–$C_4$-alkoxy and $C_1$–$C_4$-haloalkoxy;
- $R^2$ is halogen, $C_1$–$C_4$-alkyl, $C_1$–$C_4$-haloalkyl and $C_1$–$C_4$-alkoxy;
- $R^3$ is halogen, $C_1$–$C_4$-alkyl, $C_1$–$C_4$-haloalkyl, $C_1$–$C_4$-alkoxy, $C_1$–$C_4$-haloalkoxy, $C_3$–$C_6$-cycloalkyl, phenyl or phenoxy, it being possible for each of the phenyl radicals in turn to carry one to three of the following groups: halogen, $C_1$–$C_4$-alkyl, $C_1$–$C_4$-haloalkyl, $C_1$–$C_4$-alkoxy and $C_1$–$C_4$-haloalkoxy;
- $CR^a = NOR^b$, where
  - $R^a$ is hydrogen or $C_1$–$C_4$-alkyl and
  - $R^b$ is $C_1$–$C_4$-alkyl, $C_3$–$C_4$-alkenyl or $C_3$–$C_4$-alkynyl;
- n is 1, 2 or 3, it being possible for the radicals $R^3$ to be different if n is 2 or 3, and salts thereof.

Additionally, the invention relates to processes for preparing the compounds I and to compositions comprising them and to their use for controlling animal pests and harmful fungi.

The literature discloses active compounds whose general formula differs from the present compounds I in that the $R^1$ position is unsubstituted (EP-A 460 575; EP-A 585 751). Additionally, active compounds whose general formula includes the present compounds I are described in the literature (EP-A 463 488; EP-A 472 300; WO-A 92/13,830).

It is an object of the present invention to provide compounds having a broader activity spectrum and an improved activity.

We have found that this object is achieved by the compounds I defined at the outset. In addition, the invention provides processes for preparing the compounds I and compositions comprising them and their use for controlling animal pests and harmful fungi.

The present compounds I differ from the compounds known from EP-A 463 488, EP-A 472 300 and WO-A 92/13,830 in their particular combination of the groups $R^1$ and $R^3$. Specifically, it has been found that compounds of the known structural type have improved activity when they carry one of the groups mentioned under $R^1$ in position 6 and the phenyl radical is additionally substituted by at least one radical $R^3$ which increases the lipophilicity of the compound.

In general, the compounds I can be obtained by the processes described in the literature cited at the outset.

The compounds I are particularly advantageously obtained by reacting a N-hydroxyketimine IIa in an inert solvent with a benzyl compound IIIa.

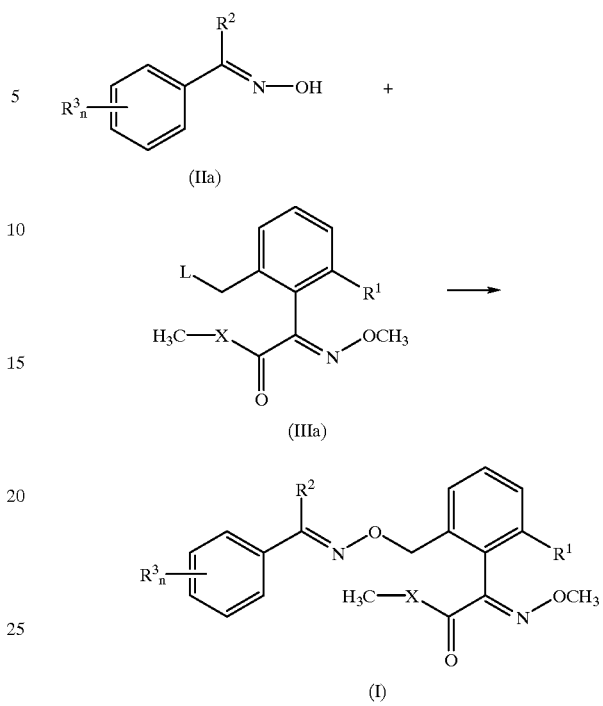

In the formula IIIa, L is a customary leaving group, for example halogen (fluorine, chlorine, bromine, iodine, in particular chlorine and bromine), $C_1$–$C_4$-alkylsulfonyl (in particular mesylate), $C_1$–$C_4$-haloalkylsulfonyl (in particular triflate) or arylsulfonyl (in particular tosylate).

The reaction of IIa with IIIa is usually carried out at from −30° C. to 120° C., preferably −10° C. to 90° C., in an inert organic solvent in the presence of a base (cf. lit. DE-A 40 20 384).

Suitable solvents are ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, and dimethyl sulfoxide, dimethylformamide and dimethylacetamide, particularly preferably tetrahydrofuran, acetonitrile, acetone and dimethylformamide. It is also possible to use mixtures of the solvents mentioned.

In general, suitable bases are inorganic compounds such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal amides, such as lithium amide, sodium amide and potassium amide, alkali metal and alkaline earth metal carbonates, such as lithium carbonate, potassium carbonate and calcium carbonate, and alkali metal bicarbonates, such as sodium bicarbonate, organometallic compounds, in particular alkali metal alkyls, such as methyllithium, butyllithium and phenyllithium, alkylmagnesium halides, such as methylmagnesium chloride, and alkali metal and alkaline earth metal alkoxides, such as sodium methoxide, sodium ethoxide, potassium ethoxide, potassium tert-butoxide and dimethoxymagnesium, moreover organic bases, for example tertiary amines, such as trimethylamine, triethylamine, triisopropylethylamine and N-methylpiperidine, pyridine, substituted pyridines such as collidine, lutidine and 4-dimethylaminopyridine, and also bicyclic amines. Particular preference is given to potassium carbonate, sodium methoxide and sodium hydride.

In general, the bases are employed in catalytic amounts, but it is also possible to employ them in equimolar amounts, in an excess or, if appropriate, as solvent.

In general, the reactants are reacted with each other in equimolar amounts. To increase the yield, it may be advantageous to employ an excess of IIa, based on IIIa.

The starting materials IIa required for preparing the compounds I are known from the literature [Bull. Soc. Chim. Fr. (1899), 69; Synth Commun. (1986), 1247; J. Agric. Food Chem. (1969), 923], or they can be prepared according to the cited literature.

The starting materials of the formula IIIa where X is O are advantageously obtained by converting a 1-bromo-2-methylbenzene of the formula IV with methyl oxalyl chloride into the corresponding α-ketophenylacetate of the formula V, converting V in a conventional manner with O-methylhydroxylamine into the corresponding oxime VI and finally halogenating VI to IIIa.

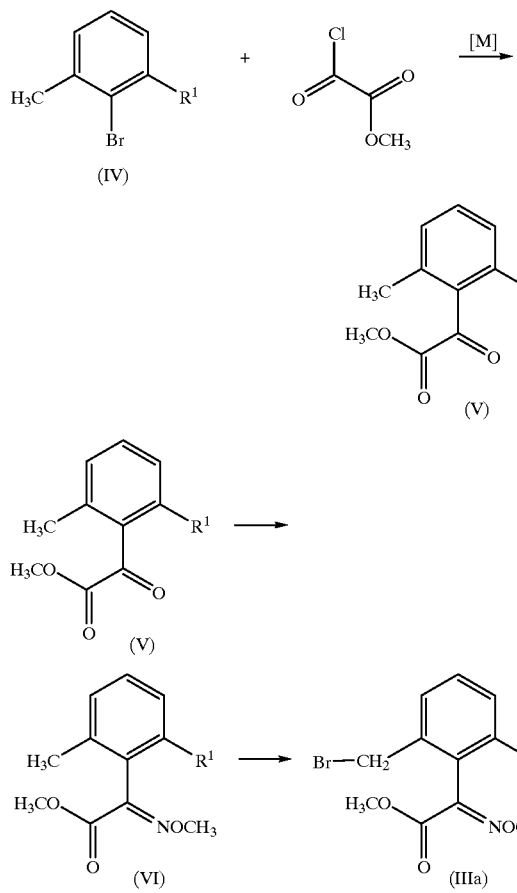

The reaction of IV with methyl oxalyl chloride is usually carried out from −78° C. to 80° C., preferably −10° C. to 60° C., in an inert organic solvent in the presence of an auxiliary reagent [M].

Suitable auxiliary reagents [M] are metals such as magnesium or metal organyls such as methyllithium, butyllithium and phenyllithium. Preference is given to using magnesium and butyllithium. In general, the auxiliary reagent is employed in at least stoichiometric amounts. It is preferably employed in amounts from 1 molar equivalent to 2 molar equivalents, in particular 1 molar equivalent to 1.3 molar equivalents, based on the phenyl derivative IV.

Suitable solvents are ethers such as diethyl ether, diisopropyl ether, tert-butyl methyl ether, dioxane, anisole and tetrahydrofuran, particularly preferably dimethyl ether or tetrahydrofuran. It is also possible to use mixtures of the solvents mentioned.

In general, the reactants are reacted with each other in equimolar amounts. To increase the yield, it may be advantageous to employ an excess of methyl oxalyl chloride, based on IV.

The reaction of the α-ketoester V with O-methylhydroxylamine is generally carried out in a customary manner at from 0° C. to 90° C., preferably 20° C. to 70° C., in an inert organic solvent; in particular, the reaction is carried out according to the conditions described in EP-A 493 711.

The halogenation of VI to IIIa is generally carried out in a conventional manner at from 0° C. to 120° C., preferably 20° C. to 110° C., in an inert organic solvent; in particular, the halogenation is carried out according to the conditions described in EP-A 385 224.

The compounds IIIa where X is NH are advantageously obtained from the corresponding esters VI by reaction with methylamine or its salt and subsequent halogenation.

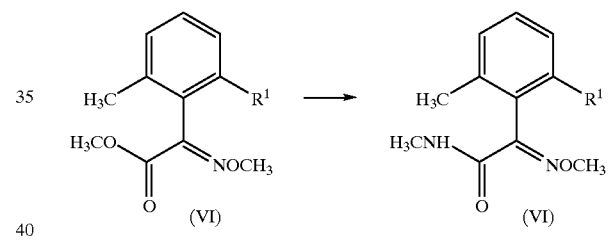

The reaction of the ester to give the amide is generally carried out in a customary manner at from 0° C. to 90° C., preferably 20° C. to 70° C., in an inert organic solvent, in particular, the reaction is carried out according to the conditions described in EP-A 477 631 and DE-A 40 20 384.

The halogenation of the amides VI is generally and in particular carried out under the conditions described for the halogenation of the esters.

Compounds IIIa where L is a leaving group other than halogen are obtained from the corresponding halides by customary etherification with a sulfonate [cf.: J. Am. Chem. Soc. (1959), 4113; HU-A 182 858].

The compounds I where $R^2$ is alkyl or haloalkyl can also be obtained by a further process by reacting a phenyl ketone IIb in an inert solvent with an O-benzylhydroxylamine IIIb.

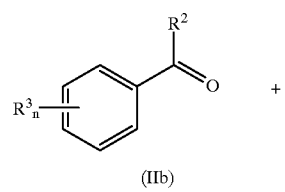

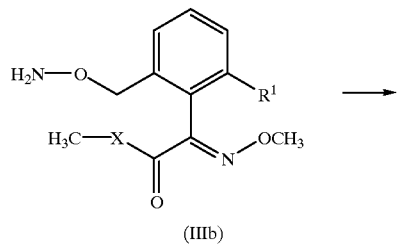

(IIIb)

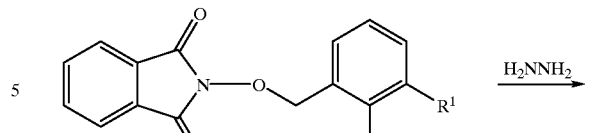

(VII)

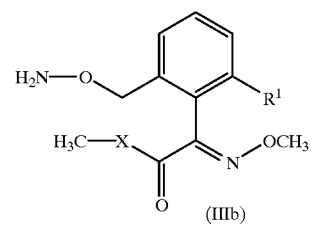

(IIIb)

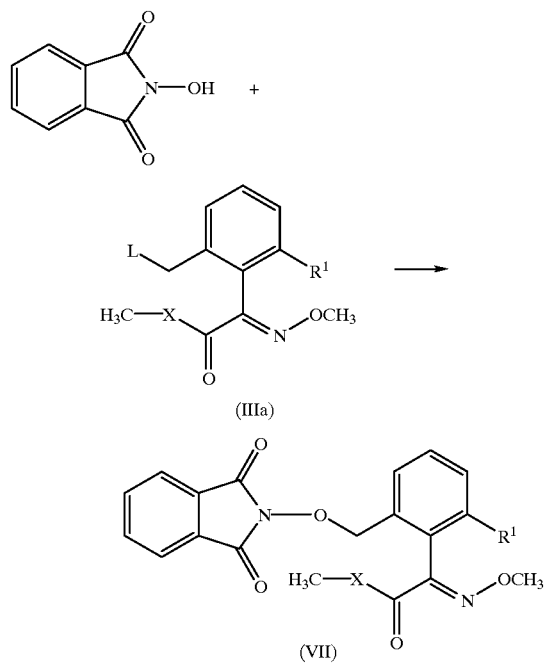

(I)

In general, this reaction is carried out in a customary manner at from −50° C. to 90° C., preferably 0° C. to 70° C., in an inert organic solvent in the presence of a base; in particular this reaction is carried out according to the conditions described in DE-A 40 20 384.

In general, the reactants are reacted with each other in equimolar amounts. To increase the yield, it may be advantageous to employ an excess of IIb, based on IIIb.

The ketones IIb required for preparing the compounds I are commercially available, are known from the literature or can be obtained by conventional processes.

The O-benzylhydroxylamines IIIb are advantageously obtained by initially etherifying a compound IIIa with N-hydroxyphthalimide and then cleaving the resulting benzyl ether VII in a conventional manner.

In general, the reaction of the benzyl compound with N-hydroxyphthalimide is carried out in a customary manner at from −30° C. to 100° C., preferably 0° C. to 70° C., in an inert organic solvent in the presence of a base; in particular, the reaction is carried out according to the conditions described in DE-A 40 20 388.

In general, the hydrolysis of the benzyl ether VII is carried out in a customary manner at from −30° C. to 90° C., preferably −10° C. to 70° C., in an inert organic solvent; in particular, the hydrolysis is carried out according to the conditions described in DE-A 40 20 388.

The reaction mixtures are worked up in a conventional manner, for example by mixing with water, phase separation and, if required, chromatographic purification of the crude products. Some of the intermediates and end products are obtained in the form of colorless or slightly brownish viscous oils which are purified or freed from volatile components under reduced pressure and at moderately elevated temperatures. If the intermediates and end products are obtained as solids, they can also be purified by recrystallization or digestion.

Owing to their C=N double bonds, the compounds I can be obtained in the preparation as E/Z isomer mixtures which can be separated into the individual compounds in a customary manner, for example by crystallization or chromatography.

However, if isomer mixtures are obtained in the synthesis, a separation is generally not necessarily required since in some cases the individual isomers can be converted into each other during preparation for use or upon use (for example under the influence of light, acids or bases). Corresponding conversions may also occur after the application, for example in the treatment of plants, in the treated plant or in the harmful fungi or animal pests to be controlled.

With regard to the C=N—OCH$_3$ double bond, preference is given to the E isomers of the compounds I with respect to their activity (configuration based on the OCH$_3$ or CH$_3$ group in relation to the COXCH$_3$ group). If isomer mixtures with regard to this double bond are formed in the synthesis, it is possible to obtain essentially pure E isomers by treating the E/Z isomer mixture with HCl in methanol [cf. EP-A 493 711]. The isomerization of the C=N—CH$_3$ double bond may be carried out at the stage of the compounds I or at the stage of the precursors of formulae VI and IIIa. Particularly preferably, the isomerization is carried out at the stage of the compounds VI.

With regard to the N=CR$^2$ double bond, preference is generally given to the E isomers of the compounds I (configuration based on the phenyl radical in relation to the OCH$_2$ group) with respect to their activity.

In the definitions of the symbols given in the above formulae, collective terms were used which generally represent the following substituents:

halogen: fluorine, chlorine, bromine and iodine;

C$_1$–C$_4$-alkyl: saturated straight-chain or branched hydrocarbon radicals having 1 to 4 carbon atoms, eg. methyl, ethyl, propyl, 1-methylethyl, butyl, 1-methylpropyl, 2-methylpropyl and 1,1-dimethylethyl;

C$_1$–C$_4$-haloalkyl: straight-chain or branched alkyl groups having 1 to 4 carbon atoms (as mentioned above), it being possible for some or all of the hydrogen atoms in these groups to be replaced by halogen atoms as mentioned above, eg. C$_1$–C$_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

C$_1$–C$_4$-alkoxy: straight-chain or branched alkyl groups having 1 to 4 carbon atoms (as mentioned above) and attached to the skeleton via an oxygen atom (—O—);

C$_1$–C$_4$-haloalkoxy: straight-chain or branched haloalkyl groups having 1 to 4 carbon atoms (as mentioned above) and attached to the skeleton via an oxygen atom (—O—);

C$_3$–C$_4$-alkenyl: unsaturated straight-chain or branched hydrocarbon radicals having 3 or 4 carbon atoms and a double bond in any position, eg. 2-propenyl, 2-butenyl, 3-butenyl, 1-methyl-2-propenyl and 2-methyl-2-propenyl;

C$_3$–C$_4$-alkynyl: straight-chain or branched hydrocarbon groups having 3 or 4 carbon atoms and a triple bond in any position, eg. 2-propynyl, 2-butynyl, 3-butynyl and 1-methyl-2-propynyl;

C$_3$–C$_6$-cycloalkyl: monocyclic saturated hydrocarbon groups having 3 to 6 carbon ring members, eg. cyclopropyl, cyclobutyl, cyclopentyl and cyclohexyl.

With regard to their biological activity, preference is given to compounds I where X is oxygen.

Furthermore, preference is given to compounds I where X is NH.

With regard to the group R$^1$, preference is given to compounds I which carry one of the following groups in this position: fluorine, chlorine, C$_1$–C$_2$-alkyl, C$_1$–C$_2$-haloalkyl, C$_1$–C$_2$-alkoxy and C$_1$–C$_2$-haloalkoxy.

Particular preference is given to compounds I where R$^1$ is fluorine or chlorine.

Additionally, preference is given to compounds I where R$^1$ is C$_1$–C$_2$-alkyl (in particular methyl), C$_1$–C$_2$-haloalkyl (in particular trifluoromethyl), C$_1$–C$_2$-alkoxy (in particular methoxy) and C$_1$–C$_2$-haloalkoxy (in particular trifluoromethoxy and difluoromethoxy).

With regard to the group R$^2$, preference is given to compounds I which carry one of the following groups in this position:

fluorine, chlorine, bromine, C$_1$–C$_2$-alkyl, C$_1$–C$_2$-haloalkyl and C$_1$–C$_4$-alkoxy.

Particular preference is given to compounds I where R$^2$ is fluorine, chlorine or bromine (in particular chlorine).

In addition, preference is given to compounds I where R$^2$ is C$_1$–C$_2$-alkyl (in particular methyl), C$_1$–C$_2$-haloalkyl (in particular trifluoromethyl) and C$_1$–C$_4$-alkoxy (in particular methoxy, ethoxy and isopropyloxy, especially methoxy).

In addition, preference is given to compounds I which carry a group R$^3$ in position 3 or 4 (in particular in position 3) of the phenyl ring.

Additionally, preference is given to compounds I which carry two groups R$^3$ in positions 3 and 4 or 3 and 5 of the phenyl ring.

Furthermore, preference is given to compounds I which carry three groups R$^3$ in positions 2, 4 and 5 of the phenyl ring.

With regard to the group R$^3$, preference is given to compounds I which carry one to three of the following groups in this position:

halogen (in particular fluorine or chlorine, especially chlorine), C$_1$–C$_2$-alkyl (especially methyl), C$_1$–C$_2$-haloalkyl (in particular difluoromethyl and trifluoromethyl, especially trifluoromethyl), C$_1$–C$_3$-alkoxy (in particular methoxy and isopropyloxy, especially methoxy), C$_1$–C$_2$-haloalkoxy (in particular difluoromethoxy and trifluoromethoxy, especially trifluormethoxy) and C$_3$–C$_6$-cycloalkyl (especially cyclopropyl), and/or one of the following groups:

phenyl or phenoxy, it being possible for each of the phenyl radicals in turn to carry one to three of the following groups: halogen (in particular fluorine or chlorine, especially chlorine), C$_1$–C$_2$-alkyl (especially methyl), C$_1$–C$_2$-haloalkyl (in particular difluoromethyl and trifluoromethyl, especially trifluoromethyl), C$_1$–C$_3$-alkoxy (in particular methoxy and isopropyloxy, especially methoxy) and C$_1$–C$_2$-haloalkoxy (in particular difluoromethoxy and trifluoromethoxy, especially trifluoromethoxy);

CR$^a$=NOR$^b$, where R$^a$ is hydrogen or C$_1$–C$_4$-alkyl (in particular C$_1$–C$_3$-alkyl, especially methyl) and R$^b$ is C$_1$–C$_4$-alkyl (in particular C$_1$–C$_3$-alkyl, especially methyl, ethyl and isopropyl), C$_3$–C$_4$-alkenyl (in particularly allyl and 2-butenyl) or C$_3$–C$_4$-alkynyl (in particular propargyl and 2-butynyl).

With respect to their biological activity, particular preference is given to the compounds I where:

X is O or NH;

R$^1$ is fluorine, chlorine, methyl, trifluoromethyl, methoxy and trifluoromethoxy;

R$^2$ is fluorine, chlorine, methyl, trifluoromethyl and methoxy;

R$^3$ is fluorine, chlorine, methyl, trifluoromethyl, methoxy, trifluoromethoxy, cyclopropyl, phenyl or phenoxy, it being possible for each of the phenyl radicals in turn to carry one to three of the following groups: fluorine, chlorine, methyl, trifluoromethyl, methoxy and trifluoromethoxy;

CH=NOCH$_3$, CH=NOCH$_2$CH$_3$, CH=NOCH$_2$CH$_2$CH$_3$, CH=NOCH(CH$_3$)$_2$, CH=NOCH$_2$CH=CH$_2$, CH=NOCH$_2$CH=CHCH$_3$, CH=NOCH$_2$C≡CH; CH=NOCH$_2$C≡CCH$_3$, C(CH$_3$)=NOCH$_3$, C(CH$_3$)=NOCH$_2$CH$_3$, C(CH$_3$)=NOCH$_2$CH$_2$CH$_3$, C(CH$_3$)=NOCH(CH$_3$)$_2$, C(CH$_3$)=NOCH$_2$CH=CH$_2$, C(CH$_3$)=NOCH$_2$CH=CHCH$_3$, C(CH$_3$)=NOCH$_2$C≡CH and C(CH$_3$)=NOCH$_2$C≡CCH$_3$;

n is 1, 2 or 3, it being possible for the radicals R$^3$ to be different if n is 2 or 3.

With respect to their biological activity, particular preference is given to the compounds I compiled in the Tables which follow. Moreover, the groups mentioned for a substituent in the Tables are, by themselves and independently of the combination in which they are mentioned, an especially preferred embodiment of the substituent in question.

Table 1

Compounds of the general formula I.A where $R^1$ is methyl, $R^2$ is chlorine and the combination of the radicals $R^3_n$ corresponds for each compound to one line of Table A

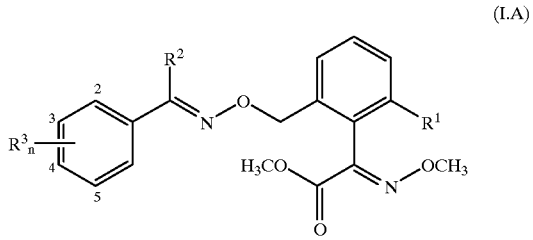

(I.A)

Table 2

Compounds of the general formula I.B where $R^1$ is methyl, $R^2$ is chlorine and the combination of the radicals $R^3_n$ corresponds for each compound to one line of Table A

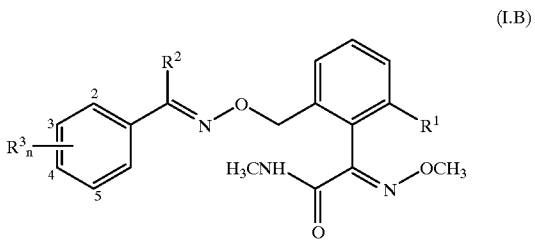

(I.B)

Table 3

Compounds of the general formula I.A where $R^1$ is fluorine, $R^2$ is methyl and the combination of the radicals $R^3_n$ corresponds for each compound to one line of Table A Table 4

Compounds of the general formula I.B where $R^1$ is fluorine, $R^2$ is methyl and the combination of the radicals $R^3_n$ corresponds for each compound to one line of Table A Table 5

Compounds of the general formula I.A where $R^1$ is chlorine, $R^2$ is methyl and the combination of the radicals $R^3_n$ corresponds for each compound to one line of Table A Table 6

Compounds of the general formula I.B where $R^1$ is chlorine, $R^2$ is methyl and the combination of the radicals $R^3_n$ corresponds for each compound to one line of Table A Table 7

Compounds of the general formula I.A where $R^1$ is methyl, $R^2$ is methyl and the combination of the radicals $R^3_n$ corresponds for each compound to one line of Table A Table 8

Compounds of the general formula I.B where $R^1$ is methyl, $R^2$ is methyl and the combination of the radicals $R^3_n$ corresponds for each compound to one line of Table A Table 9

Compounds of the general formula I.A where $R^1$ is trifluoromethyl, $R^2$ is methyl and the combination of the radicals $R^3_n$ corresponds for each compound to one line of Table A Table 10

Compounds of the general formula I.B where $R^1$ is trifluoromethyl, $R^2$ is methyl and the combination of the radicals $R^3_n$ corresponds for each compound to one line of Table A Table 11

Compounds of the general formula I.A where $R^1$ is methoxy, $R^2$ is methyl and the combination of the radicals $R^3_n$ corresponds for each compound to one line of Table A Table 12

Compounds of the general formula I.B where $R^1$ is methoxy, $R^2$ is methyl and the combination of the radicals $R^3_n$ corresponds for each compound to one line of Table A Table 13

Compounds of the general formula I.A where $R^1$ is trifluoromethoxy, $R^2$ is methyl and the combination of the radicals $R^3_n$ corresponds for each compound to one line of Table A Table 14

Compounds of the general formula I.B where $R^1$ is trifluoromethoxy, $R^2$ is methyl and the combination of the radicals $R^3_n$ corresponds for each compound to one line of Table A Table 15

Compounds of the general formula I.A where $R^1$ is fluorine, $R^2$ is ethyl and the combination of the radicals $R^3_n$ corresponds for each compound to one line of Table A Table 16

Compounds of the general formula I.B where $R^1$ is fluorine, $R^2$ is ethyl and the combination of the radicals $R^3_n$ corresponds for each compound to one line of Table A Table 17

Compounds of the general formula I.A where $R^1$ is chlorine, $R^2$ is ethyl and the combination of the radicals $R^3_n$ corresponds for each compound to one line of Table A Table 18

Compounds of the general formula I.B where $R^1$ is chlorine, $R^2$ is ethyl and the combination of the radicals $R^3_n$ corresponds for each compound to one line of Table A Table 19

Compounds of the general formula I.A where $R^1$ is methyl, $R^2$ is ethyl and the combination of the radicals $R^3_n$ corresponds for each compound to one line of Table A Table 20

Compounds of the general formula I.B where $R^1$ is methyl, $R^2$ is ethyl and the combination of the radicals $R^3_n$ corresponds for each compound to one line of Table A Table 21

Compounds of the general formula I.A where $R^1$ is trifluoromethyl, $R^2$ is ethyl and the combination of the radicals $R^3_n$ corresponds for each compound to one line of Table A Table 22

Compounds of the general formula I.B where $R^1$ is trifluoromethyl, $R^2$ is ethyl and the combination of the radicals $R^3_n$ corresponds for each compound to one line of Table A Table 23

Compounds of the general formula I.A where $R^1$ is methoxy, $R^2$ is ethyl and the combination of the radicals $R^3_n$ corresponds for each compound to one line of Table A Table 24

Compounds of the general formula I.B where $R^1$ is methoxy, $R^2$ is ethyl and the combination of the radicals $R^3_n$ corresponds for each compound to one line of Table A Table 25

Compounds of the general formula I.A where $R^1$ is trifluoromethoxy, $R^2$ is ethyl and the combination of the radicals $R^3_n$ corresponds for each compound to one line of Table Table 26

Compounds of the general formula I.B where $R^1$ is trifluoromethoxy, $R^2$ is ethyl and the combination of the radicals $R^3{}_n$ corresponds for each compound to one line of Table A Table 27

Compounds of the general formula I.A where $R^1$ is methyl, $R^2$ is methoxy and the combination of the radicals $R^3{}_n$ corresponds for each compound to one line of Table A Table 28

Compounds of the general formula I.B where $R^1$ is methyl, $R^2$ is methoxy and the combination of the radicals $R^3{}_n$ corresponds for each compound to one line of Table A Table 29

Compounds of the general formula I.A where $R^1$ is trifluoromethyl, $R^2$ is methoxy and the combination of the radicals $R^3{}_n$ corresponds for each compound to one line of Table A Table 30

Compounds of the general formula I.B where $R^1$ is trifluoromethyl, $R^2$ is methoxy and the combination of the radicals $R^3{}_n$ corresponds for each compound to one line of Table A Table 31

Compounds of the general formula I.A where $R^1$ is fluorine, $R^2$ is trifluoromethyl and the combination of the radicals $R^3{}_n$ corresponds for each compound to one line of Table A Table 32

Compounds of the general formula I.B where $R^1$ is fluorine, $R^2$ is trifluoromethyl and the combination of the radicals $R^3{}_n$ corresponds for each compound to one line of Table A Table 33

Compounds of the general formula I.A where $R^1$ is chlorine, $R^2$ is trifluoromethyl and the combination of the radicals $R^3{}_n$ corresponds for each compound to one line of Table A Table 34

Compounds of the general formula I.B where $R^1$ is chlorine, $R^2$ is trifluoromethyl and the combination of the radicals $R^3{}_n$ corresponds for each compound to one line of Table A Table 35

Compounds of the general formula I.A where $R^1$ is methyl, $R^2$ is trifluoromethyl and the combination of the radicals $R^3{}_n$ corresponds for each compound to one line of Table A Table 36

Compounds of the general formula I.B where $R^1$ is methyl, $R^2$ is trifluoromethyl and the combination of the radicals $R^3{}_n$ corresponds for each compound to one line of Table A

TABLE A

| No. | Pos. 2 | Pos. 3 | Pos. 4 | Pos. 5 |
|---|---|---|---|---|
| A.1 | H | F | H | H |
| A.2 | H | Cl | H | H |
| A.3 | H | $CH_3$ | H | H |
| A.4 | H | $CHF_2$ | H | H |
| A.5 | H | $CF_3$ | H | H |
| A.6 | H | $OCH_3$ | H | H |
| A.7 | H | $OCF_3$ | H | H |
| A.8 | H | cyclopropyl | H | H |
| A.9 | H | $C_6H_5$ | H | H |
| A.10 | H | 2-F—$C_6H_4$ | H | H |
| A.11 | H | 4-F—$C_6H_4$ | H | H |
| A.12 | H | 2-Cl—$C_6H_4$ | H | H |
| A.13 | H | 4-Cl—$C_6H_4$ | H | H |
| A.14 | H | 2-$CH_3$—$C_6H_4$ | H | H |
| A.15 | H | 3-$CH_3$—$C_6H_4$ | H | H |
| A.16 | H | O—$C_6H_5$ | H | H |
| A.17 | H | CH=$NOCH_3$ | H | H |
| A.18 | H | CH=NOCH($CH_3$) | H | H |
| A.19 | H | CH=$NOCH_2$CH=$CHCH_3$ | H | H |
| A.20 | H | C($CH_3$)=$NOCH_3$ | H | H |
| A.21 | H | C($CH_3$)=$NOCH_2CH_3$ | H | H |
| A.22 | H | C($CH_3$)=$NOCH_2$CH=$CHCH_3$ | H | H |
| A.23 | H | C($CH_3$)=$NOCH_2$C≡CH | H | H |
| A.24 | H | H | F | H |
| A.25 | H | H | Cl | H |
| A.26 | H | H | $CH_3$ | H |
| A.27 | H | H | $CHF_2$ | H |
| A.28 | H | H | $CF_3$ | H |
| A.29 | H | H | $OCH_3$ | H |
| A.30 | H | H | $OCF_3$ | H |
| A.31 | H | H | cyclopropyl | H |
| A.32 | H | H | $C_6H_5$ | H |
| A.33 | H | H | 2-F—$C_6H_4$ | H |
| A.34 | H | H | 4-F—$C_6H_4$ | H |
| A.35 | H | H | 2-Cl—$C_6H_4$ | H |
| A.36 | H | H | 4-Cl—$C_6H_4$ | H |
| A.37 | H | H | 2-$CH_3$—$C_6H_4$ | H |
| A.38 | H | H | 3-$CH_3$—$C_6H_4$ | H |
| A.39 | H | H | O—$C_6H_5$ | H |
| A.40 | H | H | CH=$NOCH_3$ | H |
| A.41 | H | H | CH=NOCH($CH_3$) | H |
| A.42 | H | H | CH=$NOCH_2$CH=$CHCH_3$ | H |
| A.43 | H | H | C($CH_3$)=$NOCH_3$ | H |

TABLE A-continued

| No. | Pos. 2 | Pos. 3 | Pos. 4 | Pos. 5 |
|---|---|---|---|---|
| A.44 | H | H | C(CH$_3$)=NOCH$_2$CH$_3$ | H |
| A.45 | H | H | C(CH$_3$)=NOCH$_2$CH=CHCH$_3$ | H |
| A.46 | H | H | C(CH$_3$)=NOCH$_2$C≡CCH$_3$ | H |
| A.47 | H | F | F | H |
| A.48 | H | Cl | F | H |
| A.49 | H | CH$_3$ | F | H |
| A.50 | H | CHF$_2$ | F | H |
| A.51 | H | CF$_3$ | F | H |
| A.52 | H | OCH$_3$ | F | H |
| A.53 | H | OCHF$_2$ | F | H |
| A.54 | H | OCF$_3$ | F | H |
| A.55 | H | cyclopropyl | F | H |
| A.56 | H | C$_6$H$_5$ | F | H |
| A.57 | H | O—C$_6$H$_5$ | F | H |
| A.58 | H | CH=NOCH$_3$ | F | H |
| A.59 | H | CH=NOCH(CH$_3$) | F | H |
| A.60 | H | CH=NOCH$_2$CH=CHCH$_3$ | F | H |
| A.61 | H | C(CH$_3$)=NOCH$_3$ | F | H |
| A.62 | H | C(CH$_3$)=NOCH$_2$CH$_3$ | F | H |
| A.63 | H | C(CH$_3$)=NOCH$_2$CH=CHCH$_3$ | F | H |
| A.64 | H | C(CH$_3$)=NOCH$_2$C≡CCH$_3$ | F | H |
| A.65 | H | F | Cl | H |
| A.66 | H | F | CH$_3$ | H |
| A.67 | H | F | CHF$_2$ | H |
| A.68 | H | F | CF$_3$ | H |
| A.69 | H | F | OCH$_3$ | H |
| A.70 | H | F | OCF$_3$ | H |
| A.71 | H | F | cyclopropyl | H |
| A.72 | H | F | C$_6$H$_5$ | H |
| A.73 | H | F | O—C$_6$H$_5$ | H |
| A.74 | H | F | CH=NOCH$_3$ | H |
| A.75 | H | F | CH=NOCH(CH$_3$) | H |
| A.76 | H | F | CH=NOCH$_2$CH=CHCH$_3$ | H |
| A.77 | H | F | C(CH$_3$)=NOCH$_3$ | H |
| A.78 | H | F | C(CH$_3$)=NOCH$_2$CH$_3$ | H |
| A.79 | H | F | C(CH$_3$)=NOCH$_2$CH=CHCH$_3$ | H |
| A.80 | H | F | C(CH$_3$)=NOCH$_2$C≡CCH$_3$ | H |
| A.81 | H | F | Cl | H |
| A.82 | H | Cl | Cl | H |
| A.83 | H | CH$_3$ | Cl | H |
| A.84 | H | CHF$_2$ | Cl | H |
| A.85 | H | CF$_3$ | Cl | H |
| A.86 | H | OCH$_3$ | Cl | H |
| A.87 | H | OCHF$_2$ | Cl | H |
| A.88 | H | OCF$_3$ | Cl | H |
| A.89 | H | cyclopropyl | Cl | H |
| A.90 | H | C$_6$H$_5$ | Cl | H |
| A.91 | H | 2-F—C$_6$H$_4$ | Cl | H |
| A.92 | H | 4-F—C$_6$H$_4$ | Cl | H |
| A.93 | H | 2-Cl—C$_6$H$_4$ | Cl | H |
| A.94 | H | 4-Cl—C$_6$H$_4$ | Cl | H |
| A.95 | H | 2-CH$_3$—C$_6$H$_4$ | Cl | H |
| A.96 | H | 3-CH$_3$—C$_6$H$_4$ | Cl | H |
| A.97 | H | O—C$_6$H$_5$ | Cl | H |
| A.98 | H | O-[2-F—C$_6$H$_4$] | Cl | H |
| A.99 | H | O-[4-F—C$_6$H$_4$] | Cl | H |
| A.100 | H | O-[2-Cl—C$_6$H$_4$] | Cl | H |
| A.101 | H | O-[4-Cl—C$_6$H$_4$] | Cl | H |
| A.102 | H | O-[2-CH$_3$—C$_6$H$_4$] | Cl | H |
| A.103 | H | O-[3-CH$_3$—C$_6$H$_4$] | Cl | H |
| A.104 | H | CH=NOCH$_3$ | Cl | H |
| A.105 | H | CH=NOCH(CH$_3$) | Cl | H |
| A.106 | H | CH=NOCH$_2$CH=CHCH$_3$ | Cl | H |
| A.107 | H | C(CH$_3$)=NOCH$_3$ | Cl | H |
| A.108 | H | C(CH$_3$)=NOCH$_2$CH$_3$ | Cl | H |
| A.109 | H | C(CH$_3$)=NOCH$_2$CH=CHCH$_3$ | Cl | H |
| A.110 | H | C(CH$_3$)=NOCH$_2$C≡CCH$_3$ | Cl | H |
| A.111 | H | Cl | F | H |
| A.112 | H | Cl | CH$_3$ | H |
| A.113 | H | Cl | CHF$_2$ | H |
| A.114 | H | Cl | CF$_3$ | H |
| A.115 | H | Cl | OCH$_3$ | H |
| A.116 | H | Cl | OCHF$_2$ | H |
| A.117 | H | Cl | OCF$_3$ | H |
| A.118 | H | Cl | cyclopropyl | H |
| A.119 | H | Cl | C$_6$H$_5$ | H |
| A.120 | H | Cl | 2-F—C$_6$H$_4$ | H |

TABLE A-continued

| No. | Pos. 2 | Pos. 3 | Pos. 4 | Pos. 5 |
|---|---|---|---|---|
| A.121 | H | Cl | 4-F—$C_6H_4$ | H |
| A.122 | H | Cl | 2-Cl—$C_6H_4$ | H |
| A.123 | H | Cl | 4-Cl—$C_6H_4$ | H |
| A.124 | H | Cl | 2-$CH_3$—$C_6H_4$ | H |
| A.125 | H | Cl | 3-$CH_3$—$C_6H_4$ | H |
| A.126 | H | Cl | O—$C_6H_5$ | H |
| A.127 | H | Cl | CH=$NOCH_3$ | H |
| A.128 | H | Cl | CH=$NOCH(CH_3)$ | H |
| A.129 | H | Cl | CH=$NOCH_2CH$=$CHCH_3$ | H |
| A.130 | H | Cl | $C(CH_3)$=$NOCH_3$ | H |
| A.131 | H | Cl | $C(CH_3)$=$NOCH_2CH_3$ | H |
| A.132 | H | Cl | $C(CH_3)$=$NOCH_2CH$=$CHCH_3$ | H |
| A.133 | H | Cl | $C(CH_3)$=$NOCH_2C$≡$CCH_3$ | H |
| A.134 | H | F | $CH_3$ | H |
| A.135 | H | Cl | $CH_3$ | H |
| A.136 | H | $CH_3$ | $CH_3$ | H |
| A.137 | H | $CF_3$ | $CH_3$ | H |
| A.138 | H | $OCH_3$ | $CH_3$ | H |
| A.139 | H | $OCF_3$ | $CH_3$ | H |
| A.140 | H | cyclopropyl | $CH_3$ | H |
| A.141 | H | $C_6H_5$ | $CH_3$ | H |
| A.142 | H | 2-F—$C_6H_4$ | $CH_3$ | H |
| A.143 | H | 2-$CH_3$—$C_6H_4$ | $CH_3$ | H |
| A.144 | H | 3-$CF_3$—$C_6H_4$ | $CH_3$ | H |
| A.145 | H | 4-$OCH_3$—$C_6H_4$ | $CH_3$ | H |
| A.146 | H | 3-$OCF_3$—$C_6H_4$ | $CH_3$ | H |
| A.147 | H | O—$C_6H_5$ | $CH_3$ | H |
| A.148 | H | CH=$NOCH_3$ | $CH_3$ | H |
| A.149 | H | CH=$NOCH(CH_3)$ | $CH_3$ | H |
| A.150 | H | CH=$NOCH_2CH$=$CHCH_3$ | $CH_3$ | H |
| A.151 | H | $C(CH_3)$=$NOCH_3$ | $CH_3$ | H |
| A.152 | H | $C(CH_3)$=$NOCH_2CH$=$CHCH_3$ | $CH_3$ | H |
| A.153 | H | $C(CH_3)$=$NOCH_2C$≡$CCH_3$ | $CH_3$ | H |
| A.154 | H | $CH_3$ | F | H |
| A.155 | H | $CH_3$ | Cl | H |
| A.156 | H | $CH_3$ | $CF_3$ | H |
| A.157 | H | $CH_3$ | $OCH_3$ | H |
| A.158 | H | $CH_3$ | $OCF_3$ | H |
| A.159 | H | $CH_3$ | cyclopropyl | H |
| A.160 | H | $CH_3$ | $C_6H_5$ | H |
| A.161 | H | $CH_3$ | O—$C_6H_5$ | H |
| A.162 | H | $CH_3$ | CH=$NOCH_3$ | H |
| A.163 | H | $CH_3$ | CH=$NOCH(CH_3)$ | H |
| A.164 | H | $CH_3$ | CH=$NOCH_2CH$=$CHCH_3$ | H |
| A.165 | H | $CH_3$ | $C(CH_3)$=$NOCH_3$ | H |
| A.166 | H | $CH_3$ | $C(CH_3)$=$NOCH_2CH$=$CHCH_3$ | H |
| A.167 | H | $CH_3$ | $C(CH_3)$=$NOCH_2C$≡$CCH_3$ | H |
| A.168 | H | F | $CF_3$ | H |
| A.169 | H | Cl | $CF_3$ | H |
| A.170 | H | $CH_3$ | $CF_3$ | H |
| A.171 | H | $CF_3$ | $CF_3$ | H |
| A.172 | H | $OCH_3$ | $CF_3$ | H |
| A.173 | H | $OCF_3$ | $CF_3$ | H |
| A.174 | H | cyclopropyl | $CF_3$ | H |
| A.175 | H | $C_6H_5$ | $CF_3$ | H |
| A.176 | H | O—$C_6H_5$ | $CF_3$ | H |
| A.177 | H | CH=$NOCH_3$ | $CF_3$ | H |
| A.178 | H | CH=$NOCH(CH_3)$ | $CF_3$ | H |
| A.179 | H | CH=$NOCH_2CH$=$CHCH_3$ | $CF_3$ | H |
| A.180 | H | $C(CH_3)$=$NOCH_3$ | $CF_3$ | H |
| A.181 | H | $C(CH_3)$=$NOCH_2CH$=$CHCH_3$ | $CF_3$ | H |
| A.182 | H | $C(CH_3)$=$NOCH_2C$≡$CCH_3$ | $CF_3$ | H |
| A.183 | H | $CF_3$ | F | H |
| A.184 | H | $CF_3$ | Cl | H |
| A.185 | H | $CF_3$ | $CH_3$ | H |
| A.186 | H | $CF_3$ | $OCH_3$ | H |
| A.187 | H | $CF_3$ | $OCF_3$ | H |
| A.188 | H | $CF_3$ | cyclopropyl | H |
| A.189 | H | $CF_3$ | $C_6H_5$ | H |
| A.190 | H | $CF_3$ | O—$C_6H_5$ | H |
| A.191 | H | $CF_3$ | CH=$NOCH_3$ | H |
| A.192 | H | $CF_3$ | CH=$NOCH(CH_3)$ | H |
| A.193 | H | $CF_3$ | CH=$NOCH_2CH$=$CHCH_3$ | H |
| A.194 | H | $CF_3$ | $C(CH_3)$=$NOCH_3$ | H |
| A.195 | H | $CF_3$ | $C(CH_3)$=$NOCH_2CH$=$CHCH_3$ | H |
| A.196 | H | $CF_3$ | $C(CH_3)$=$NOCH_2C$≡$CCH_3$ | H |
| A.197 | H | F | $OCH_3$ | H |

TABLE A-continued

| No. | Pos. 2 | Pos. 3 | Pos. 4 | Pos. 5 |
|---|---|---|---|---|
| A.198 | H | Cl | OCH$_3$ | H |
| A.199 | H | CH$_3$ | OCH$_3$ | H |
| A.200 | H | CF$_3$ | OCH$_3$ | H |
| A.201 | H | OCH$_3$ | OCH$_3$ | H |
| A.202 | H | OCF$_3$ | OCH$_3$ | H |
| A.203 | H | cyclopropyl | OCH$_3$ | H |
| A.204 | H | C$_6$H$_5$ | OCH$_3$ | H |
| A.205 | H | O—C$_6$H$_5$ | OCH$_3$ | H |
| A.206 | H | CH=NOCH$_3$ | OCH$_3$ | H |
| A.207 | H | CH=NOCH(CH$_3$) | OCH$_3$ | H |
| A.208 | H | CH=NOCH$_2$CH=CHCH$_3$ | OCH$_3$ | H |
| A.209 | H | C(CH$_3$)=NOCH$_3$ | OCH$_3$ | H |
| A.210 | H | C(CH$_3$)=NOCH$_2$CH=CHCH$_3$ | OCH$_3$ | H |
| A.211 | H | C(CH$_3$)=NOCH$_2$CH≡CCH$_3$ | OCH$_3$ | H |
| A.212 | H | OCH$_3$ | F | H |
| A.213 | H | OCH$_3$ | Cl | H |
| A.214 | H | OCH$_3$ | CH$_3$ | H |
| A.215 | H | OCH$_3$ | CF$_3$ | H |
| A.216 | H | OCH$_3$ | OCF$_3$ | H |
| A.217 | H | OCH$_3$ | cyclopropyl | H |
| A.218 | H | OCH$_3$ | C$_6$H$_5$ | H |
| A.219 | H | OCH$_3$ | O—C$_6$H$_5$ | H |
| A.220 | H | OCH$_3$ | CH=NOCH$_3$ | H |
| A.221 | H | OCH$_3$ | CH=NOCH(CH$_3$) | H |
| A.222 | H | OCH$_3$ | CH=NOCH$_2$CH=CHCH$_3$ | H |
| A.223 | H | OCH$_3$ | C(CH$_3$)=NOCH$_3$ | H |
| A.224 | H | OCH$_3$ | C(CH$_3$)=NOCH$_2$CH=CHCH$_3$ | H |
| A.225 | H | OCH$_3$ | C(CH$_3$)=NOCH$_2$C≡CCH$_3$ | H |
| A.226 | H | C(CH$_3$)=NOCH$_3$ | OCF$_3$ | H |
| A.227 | H | C(CH$_3$)=NOCH$_2$CH=CHCH$_3$ | OCF$_3$ | H |
| A.228 | H | C(CH$_3$)=NOCH$_2$C≡CCH$_3$ | OCF$_3$ | H |
| A.229 | H | OCF$_3$ | F | H |
| A.230 | H | OCF$_3$ | Cl | H |
| A.231 | H | OCF$_3$ | CH$_3$ | H |
| A.232 | H | OCF$_3$ | CF$_3$ | H |
| A.233 | H | OCF$_3$ | OCH$_3$ | H |
| A.234 | H | F | H | F |
| A.235 | H | Cl | H | F |
| A.236 | H | CH$_3$ | H | F |
| A.237 | H | CHF$_2$ | H | F |
| A.238 | H | CF$_3$ | H | F |
| A.239 | H | OCH$_3$ | H | F |
| A.240 | H | OCF$_3$ | H | F |
| A.241 | H | cyclopropyl | H | F |
| A.242 | H | C$_6$H$_5$ | H | F |
| A.243 | H | O—C$_6$H$_5$ | H | F |
| A.244 | H | CH=NOCH$_3$ | H | F |
| A.245 | H | CH=NOCH(CH$_3$) | H | F |
| A.246 | H | CH=NOCH$_2$CH=CHCH$_3$ | H | F |
| A.247 | H | C(CH$_3$)=NOCH$_3$ | H | F |
| A.248 | H | C(CH$_3$)=NOCH$_2$CH$_3$ | H | F |
| A.249 | H | C(CH$_3$)=NOCH$_2$CH=CHCH$_3$ | H | F |
| A.250 | H | C(CH$_3$)=NOCH$_2$C≡CCH$_3$ | H | F |
| A.251 | H | F | H | O—C$_6$H$_5$ |
| A.252 | H | Cl | H | Cl |
| A.253 | H | CH$_3$ | H | Cl |
| A.254 | H | CHF$_2$ | H | Cl |
| A.255 | H | CF$_3$ | H | Cl |
| A.256 | H | OCH$_3$ | H | Cl |
| A.257 | H | OCF$_3$ | H | Cl |
| A.258 | H | cyclopropyl | H | Cl |
| A.259 | H | C$_6$H$_5$ | H | Cl |
| A.260 | H | O—C$_6$H$_5$ | H | Cl |
| A.261 | H | CH=NOCH$_3$ | H | Cl |
| A.262 | H | CH=NOCH(CH$_3$) | H | Cl |
| A.263 | H | CH=NOCH$_2$CH=CHCH$_3$ | H | Cl |
| A.264 | H | C(CH$_3$)=NOCH$_3$ | H | Cl |
| A.265 | H | C(CH$_3$)=NOCH$_2$CH$_3$ | H | Cl |
| A.266 | H | C(CH$_3$)=NOCH$_2$CH=CHCH$_3$ | H | Cl |
| A.267 | H | C(CH$_3$)=NOCH$_2$C≡CCH$_3$ | H | Cl |
| A.268 | H | CH$_3$ | H | CH$_3$ |
| A.269 | H | CF$_3$ | H | CH$_3$ |
| A.270 | H | OCH$_3$ | H | CH$_3$ |
| A.271 | H | OCF$_3$ | H | CH$_3$ |
| A.272 | H | cyclopropyl | H | CH$_3$ |
| A.273 | H | C$_6$H$_5$ | H | CH$_3$ |
| A.274 | H | O—C$_6$H$_5$ | H | CH$_3$ |

TABLE A-continued

| No. | Pos. 2 | Pos. 3 | Pos. 4 | Pos. 5 |
| --- | --- | --- | --- | --- |
| A.275 | H | CH=NOCH$_3$ | H | CH$_3$ |
| A.276 | H | CH=NOCH(CH$_3$) | H | CH$_3$ |
| A.277 | H | CH=NOCH$_2$CH=CHCH$_3$ | H | CH$_3$ |
| A.278 | H | C(CH$_3$)=NOCH$_3$ | H | CH$_3$ |
| A.279 | H | C(CH$_3$)=NOCH$_2$CH=CHCH$_3$ | H | CH$_3$ |
| A.280 | H | C(CH$_3$)=NOCH$_2$C≡CCH$_3$ | H | CH$_3$ |
| A.281 | H | CF$_3$ | H | CF$_3$ |
| A.282 | H | OCH$_3$ | H | CF$_3$ |
| A.283 | H | OCF$_3$ | H | CF$_3$ |
| A.284 | H | cyclopropyl | H | CF$_3$ |
| A.285 | H | C$_6$H$_5$ | H | CF$_3$ |
| A.286 | H | 2-F—C$_6$H$_4$ | H | CF$_3$ |
| A.287 | H | 2-CH$_3$—C$_6$H$_4$ | H | CF$_3$ |
| A.288 | H | 3-CF$_3$—C$_6$H$_4$ | H | CF$_3$ |
| A.289 | H | 4-OCH$_3$—C$_6$H$_4$ | H | CF$_3$ |
| A.290 | H | 3-OCF$_3$—C$_6$H$_4$ | H | CF$_3$ |
| A.291 | H | O—C$_6$H$_5$ | H | CF$_3$ |
| A.292 | H | O-[4-F—C$_6$H$_4$] | H | CF$_3$ |
| A.293 | H | O-[2-Cl—C$_6$H$_4$] | H | CF$_3$ |
| A.294 | H | O-[2-CH$_3$—C$_6$H$_4$] | H | CF$_3$ |
| A.295 | H | CH=NOCH$_3$ | H | CF$_3$ |
| A.296 | H | CH=NOCH(CH$_3$) | H | CF$_3$ |
| A.297 | H | CH=NOCH$_2$CH=CHCH$_3$ | H | CF$_3$ |
| A.298 | H | C(CH$_3$)=NOCH$_3$ | H | CF$_3$ |
| A.299 | H | C(CH$_3$)=NOCH$_2$CH=CHCH$_3$ | H | CF$_3$ |
| A.300 | H | C(CH$_3$)=NOCH$_2$C≡CCH$_3$ | H | CF$_3$ |
| A.301 | H | OCH$_3$ | H | OCH$_3$ |
| A.302 | H | OCF$_3$ | H | OCH$_3$ |
| A.303 | H | cyclopropyl | H | OCH$_3$ |
| A.304 | H | C$_6$H$_5$ | H | OCH$_3$ |
| A.305 | H | O—C$_6$H$_5$ | H | OCH$_3$ |
| A.306 | H | CH=NOCH$_3$ | H | OCH$_3$ |
| A.307 | H | CH=NOCH(CH$_3$) | H | OCH$_3$ |
| A.308 | H | CH=NOCH$_2$CH=CHCH$_3$ | H | OCH$_3$ |
| A.309 | H | C(CH$_3$)=NOCH$_3$ | H | OCH$_3$ |
| A.310 | H | C(CH$_3$)=NOCH$_2$CH=CHCH$_3$ | H | OCH$_3$ |
| A.311 | H | C(CH$_3$)=NOCH$_2$C≡CCH$_3$ | H | OCH$_3$ |
| A.312 | H | cyclopropyl | H | OCF$_3$ |
| A.313 | H | C$_6$H$_5$ | H | OCF$_3$ |
| A.314 | H | O—C$_6$H$_5$ | H | OCF$_3$ |
| A.315 | H | CH=NOCH$_3$ | H | OCF$_3$ |
| A.316 | H | CH=NOCH(CH$_3$) | H | OCF$_3$ |
| A.317 | H | CH=NOCH$_2$CH=CHCH$_3$ | H | OCF$_3$ |
| A.318 | H | C(CH$_3$)=NOCH$_3$ | H | OCF$_3$ |
| A.319 | H | C(CH$_3$)=NOCH$_2$CH=CHCH$_3$ | H | OCF$_3$ |
| A.320 | H | C(CH$_3$)=NOCH$_2$C≡CCH$_3$ | H | OCF$_3$ |
| A.321 | CH$_3$ | H | H | H |
| A.322 | Cl | H | H | H |
| A.323 | F | H | H | H |
| A.324 | CF$_3$ | H | H | H |
| A.325 | Cl | H | Cl | Cl |
| A.326 | CH$_3$ | CF$_3$ | H | H |
| A.327 | Cl | CF$_3$ | H | H |
| A.328 | F | CF$_3$ | H | H |
| A.329 | CH$_3$ | H | CF$_3$ | H |
| A.330 | CH$_3$ | H | Cl | H |
| A.331 | F | H | CF$_3$ | H |
| A.332 | F | H | F | H |

The compounds I are suitable as fungicides. They have excellent activity against a broad spectrum of phytopathogenic fungi, in particular from the classes of the Ascomycetes, Deuteromycetes, Phycomycetes and Basidiomycetes. Some of them act systemically and can be employed in crop protection as foliar- and soil-acting fungicides.

They are especially important for controlling a large number of fungi in a variety of crop plants such as wheat, rye, barley, oats, rice, maize, lawn, bananas, cotton, soy, coffee, sugar cane, grapevines, fruit species, ornamentals and vegetable species such as cucumbers, beans, tomatoes, potatoes and curcubits, and also in the seeds of these plants.

Specifically, they are suitable for controlling the following plant diseases:

Alternaria species in vegetables and fruit,
*Botrytis cinerea* (gray mold) in strawberries, vegetables, ornamentals and grapevines,
*Cercospora arachidicola* in groundnuts,
*Erysiphe cichoracearum* and *Sphaerotheca fuliginea* in curcubits,
*Erysiphe graminis* (powdery mildew) in cereals,
Fusarium and Verticillium species in a variety of plants,
Helminthosporium species in cereals,
Mycosphaerella species in bananas,
*Phytophthora infestans* in potatoes and tomatoes,
*Plasmopara viticola* in grapevines,
*Podosphaera leucotricha* in apples,

*Pseudocercosporella herpotrichoides* in wheat and barley,
*Pseudocercosporella* species in hops and cucumbers,
*Puccinia* species in cereals,
*Pyricularia oryzae* in rice,
*Rhizoctonia* species in cotton, rice and lawn,
*Septoria nodorum* in wheat,
*Uncinula necator* in grapevines,
*Ustilago* species in cereals and sugar cane, and
*Venturia inaequalis* (scab) in apples.

In addition, the compounds I are suitable for controlling harmful fungi such as *Paecilomyces variotii* in the protection of materials (for example wood, paper, paint dispersions, fibers or tissues) and in the protection of stored products.

The compounds I are employed by treating the fungi or the plants, seeds, materials or the soil to be proteced from being attacked by fungi with a fungicidally effective amount of the active compounds. The application is carried out before or after the infection of the materials, plants or seeds by the fungi.

The fungicidal compositions generally comprise from 0.1 to 95, preferably from 0.5 to 90%, by weight of active compound.

For use in crop protection, the application rates are, depending in each case on the kind of desired effect, from 0.01 to 2.0 kg of active compound per ha.

The treatment of seeds generally requires active compound quantities from 0.001 to 0.1 g, preferably from 0.01 to 0.05 g, per kilogram of seeds.

For use in the protection of materials or stored products, the active compound application rate depends on the kind of application area and desired effect. Customary application rates in the protection of materials are, for example, from 0.001 g to 2 kg, preferably from 0.005 g to 1 kg, of active compound per cubic meter of treated material.

The compounds of the formula I are also suitable for the efficient control of animal pests from the classes of insects, arachnids and nematodes. They can be used in crop protection and in the hygiene sector, in the protection of materials and the veterinary sector for controlling animal pests. They are particularly suitable for controlling the following animal pests:

insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis,* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllotreta chrysocephala,* Phyllophaga sp., *Phyllopertha horticola, Phyllotreta nemorum, Phyllotreta striolata, Popillia japonica, Sitona lineatus* and *Sitophilus granaria,* dipterans (Diptera), for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa,* thrips (Thysanoptera), for example *Frankliniella fusca, Frankliniella occidentalis, Frankliniella tritici, Scirtothrips citri, Thrips oryzae, Thrips palmi* and *Thrips tabaci,* hymenopterans (Hymenoptera), for example *Athalia rosae, Atta cephalotes, Atta sexdens, Atta texana, Hoplocampa minuta, Hoplocampa testudinea, Monomorium pharaonis, Solenopsis geminata* and *Solenopsis invicta,* heteropterans (Heteroptera), for example *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor,* homopterans (Homoptera), for example *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis* radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum and Viteus vitifolii, termites (Isoptera), for example *Calotermes flavicollis, Leucotermes flavipes, Reticulitermes lucifugus* and *Termes natalensis,* orthopterans (Orthoptera), for example *Acheta domestica, Blatta orientalis, Blattella germanica, Forficula auricularia, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus,* arachnoidea such as arachnids (Acarina), for example *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius* and *Tetranychus urticae,* nematodes such as root gall nematodes, for example *Meloidogyne hapla, Meloidogyne incognita, Meloidogyne javanica,* cyst-forming nematodes, for example *Globodera rostochiensis, Heterodera avenae, Heterodera glycines, Heterodera schachtii, Heterodera trifolii,* stem and leaf nematodes, for example *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi.*

For controlling animal pests under free-range conditions, the application rate of active compound is from 0.1 to 2.0, preferably from 0.2 to 1.0, kg/ha.

The compounds I can be converted into the customary formulations, for example solutions, emulsions, suspensions, dusts, powders, pastes and granules. The application form depends on the particular intended use; in each case it should guarantee a fine and even distribution of the compound according to the invention.

The formulations are prepared in a known manner, for example by extending the active compound with solvents and/or carriers, if desired using emulsifiers and dispersants, where, if water is used as a diluent, other organic solvents can also be used as auxiliary solvents. Suitable auxiliaries for this purpose are essentially: solvents such as aromatics (for example xylene), chlorinated aromatics (for example chlorobenzenes), paraffins (for example petroleum fractions), alcohols (for example methanol, butanol), ketones (for example cyclohexanone), amines (for example ethanolamine, dimethylformamide) and water; carriers such as ground natural minerals (for example kaolins, argillaceous earths, talc, chalk) and ground synthetic minerals (for example finely divided silica, silicates); emulsifiers such as nonionic and anionic emulsifiers (for example polyoxyethylene fatty alcohol ethers, alkylsulfonates and arylsulfonates) and dispersants such as lignosulfite waste liquors and methylcellulose.

Suitable surfactants are the alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and alkali metal salts and alkaline earth metal salts thereof, salts of sulfated fatty alcohol glycol ethers, condensation products of sulfonated naphthalene and naphthalene derivatives with formaldehyde, condensation products of naphthalene or of naphthalenesulfonic acid with phenol and formaldehyde, polyoxyethylene octylphenol ethers, ethoxylated isooctylphenol, octylphenol and nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Suitable for preparing directly sprayable solutions, emulsions, pastes or oil dispersions are petroleum fractions having medium to high boiling points, such as kerosene or diesel fuel, furthermore coal-tar oils and oils of plant or animal origin, aliphatic, cyclic and aromatic hydrocarbons, for example benzene, toluene, xylene, paraffin, tetrahydronaphthalene, alkylated naphthalenes or derivatives thereof, methanol, ethanol, propanol, butanol, chloroform, carbon tetrachloride, cyclohexanol, cyclohexanone, chlorobenzene, isophorone, strongly polar solvents, for example dimethylformamide, dimethyl sulfoxide, N-methylpyrrolidone, and water.

Powders, compositions for broadcasting and dusts can be prepared by mixing or joint grinding of the active substances with a solid carrier.

Granules, for example coated granulates, impregnated granules and homogenous granules, can be prepared by binding the active ingredients to solid carriers. Solid carriers are, for example, mineral earths, such as silica gel, silicas, silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas and products of plant origin, such as cereal meal, tree bark meal, wood meal and nutshell meal, cellulose powders and other solid carriers.

The formulations generally comprise from 0.01 to 95% by weight, preferably from 0.1 to 90% by weight, of the active compound. The active compounds are employed in a purity of from 90% to 100%, preferably from 95% to 100% (according to NMR spectrum).

Examples of formulations are:

I. 5 parts by weight of a compound according to the invention are thoroughly mixed with 95 parts by weight of finely divided kaolin. This affords a dusting composition comprising 5% by weight of the active compound.

II. 30 parts by weight of a compound according to the invention are thoroughly mixed with a mixture of 92 parts by weight of pulverulent silica gel and 8 parts by weight of paraffin oil which had been sprayed onto the surface of this silica gel. This affords an active compound preparation having good adhesive properties (active compound content 23% by weight).

III. 10 parts by weight of a compound according to the invention are dissolved in a mixture comprising 90 parts by weight of xylene, 6 parts by weight of the addition product of 8 to 10 mol of ethylene oxide to 1 mol of oleic acid N-monoethanolamide, 2 parts by weight of the calcium salt of dodecylbenzenesulfonic acid and 2 parts by weight of the addition product of 40 mol of ethylene oxide to 1 mol of castor oil (active compound content 9% by weight).

IV. 20 parts by weight of a compound according to the invention are dissolved in a mixture comprising 60 parts by weight of cyclohexanone, 30 parts by weight of isobutanol, 5 parts by weight of the addition product of 7 mol of ethylene oxide to 1 mol of isooctylphenol and 5 parts by weight of the addition product of 40 mol of ethylene oxide to 1 mol of castor oil (active compound content 16% by weight).

V. 80 parts by weight of a compound according to the invention are mixed well with 3 parts by weight of the sodium salt of diisobutylnaphthalene-α-sulfonic acid, 10 parts by weight of the sodium salt of a lignosulfonic acid from a sulfite waste liquor and 7 parts by weight of pulverulent silica gel, and ground in a hammer mill (active compound content 80% by weight).

VI. 90 parts by weight of a compound according to the invention are mixed with 10 parts by weight of N-methyl-α-pyrrolidone, affording a solution which is suitable for use in the form of very small drops (active compound 90% by weight).

VII. 20 parts by weight of a compound according to the invention are dissolved in a mixture comprising 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. The solution is poured into 100,000 parts by weight of water and finely dispersed therein, affording an aqueous dispersion comprising 0.02% by weight of active compound.

VIII. 20 parts by weight of a compound according to the invention are mixed well with 3 parts by weight of the sodium salt of diisobutylnaphthalene-α-sulfonic acid, 17 parts by weight of the sodium salt of a lignosulfonic acid from a sulfite waste liquor and 60 parts by weight of pulverulent silica gel, and ground in a hammer mill. The mixture is finely dispersed in 20,000 parts by weight of water, affording a spray liquor comprising 0.1% by weight of active compound.

The active compounds can be applied as such, in the form of their formulations or in the application forms prepared therefrom, for example in the form of directly sprayable solutions, powders, suspensions or dispersions, emulsions, oil dispersions, pastes, dusts, compositions for broadcasting or granules, by spraying, atomizing, dusting, broadcasting or watering. The application forms depend entirely on the intended uses; in each case they should if possible guarantee finest distribution of the active compounds according to the invention.

Aqueous use forms can be prepared from emulsion concentrates, pastes or wettable powders (spray powders, oil dispersions) by addition of water. To prepare emulsions, pastes or oil dispersions, the substances can be homogenized in water as such or dissolved in an oil or solvent, by means of wetting agents, tackifiers, dispersants or emulsifiers.

However, concentrates comprising active compound, wetting agent, tackifier, dispersant or emulsifier and possibly solvent or oil which are suitable for dilution with water can also be prepared.

The active compound concentrations in the ready-to-use preparations can be varied over a relatively wide range. In general, they are from 0.0001 to 10%, preferably from 0.01 to 1%.

It is also possible to use the active compounds with good success in the ultra-low-volume process (ULV), it being possible to apply formulations comprising more than 95% by weight of active compound or even the active compound without additives.

It is possible to admix oils of various types, herbicides, fungicides, other pesticides, or bactericides to the active compounds, even, if appropriate, immediately prior to application (tank mix). These agents may be admixed with the compositions according to the invention at a weight ratio from 1:10 to 10:1.

The compounds according to the invention in the use form as fungicides may also be present together with other active compounds, for example with herbicides, insecticides, growth regulators, fungicides or else with fertilizers. In many cases, a mixture of the compounds I or of the compositions comprising them in the use form as fungicide with other fungicides results in a widened fungicidal spectrum of activity.

The following list of fungicides together with which the compounds according to the invention can be used is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl)disulfide;

nitro derivatives, such as dinitro(1-methylheptyl)phenyl crotonate, 2-sec-butyl-4,6-dinitrophenyl-3,3-dimethyl acrylate, 2-sec-butyl-4,6-dinitrophenylisopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(furyl-(2)) benzimidazole, 2-(thiazolyl)-(4))benzimidazole, N-(1, 1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfuric diamide, 5-ethoxy-3-trichloromethyl-1, 2,3-thiadiazole, 2-thiocyanatomethylthiobenzothiazole, 1,4-dichloro-2, 5-dimethoxybenzene, 4-(2-chlorophenylhydrazono)-3-methyl-5-isoxazolone, pyridine 2-thio-1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine-4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxanilide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazine-1,4-diyl-bis-(1-(2,2,2-trichloroethyl) formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethyl-morpholine, N-[3-(p-tert-butylphenyl)-2-methylpropyl]-piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxymethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methyl-pyrimidine, bis(p-chlorophenyl)-3-pyridinemethanol, 1,2-bis-(3-ethoxycarbonyl-2-thioureido)-benzene, 1,2-bis-(3-methoxycarbonyl-2-thioureido)benzene, strobilurins such as methyl E-methoxyimino-[α-(o-tolyloxy)-o-tolyl]acetate, methyl-E-2-{2-[6-(2-cyano-phenoxy)pyrimidin-4-yloxy]phenyl}-3-methoxyacrylate, N-methyl-E-methoxyimino-[ α-(2 -phenoxyphenyl) ]-acetamide, N-methyl-E-methoxyimino-[ α-(2,5-dimethylphenoxy)-o-tolyl]-acetamide, anilinopyrimidines, such as N-(4,6-dimethylpyrimidin-2-yl)-aniline, N-[4-methyl-6-(1-propinyl)-pyrimidin-2-yl]-aniline, N-[4-methyl-6-cyclopropyl-pyrimidin-2-yl]-aniline, phenylpyrroles such as 4-(2,2-difluoro-1,3-benzodioxol-4-yl)-pyrrole-3-carbonitrile, cinnamides, such as 3-(4-chlorophenyl)-3-(3,4-dimethoxyphenyl)acryloyl]morpholine, and a variety of fungicides, such as dodecylguanidine acetate, 3-[3-(3,5-dimethyl-2-oxycyclohexyl)-2-hydroxyethyl]-glutarimide, hexachlorobenzene, methyl-N-(2,6-dimethylphenyl)-N-( 2-furoyl)-DL-alaninate, DL-N-(2,6-dimethylphenyl)-N-(2'-methoxyacetyl)alanine methyl ester, (N-(2,6-dimethylphenyl)-N-chloroacetyl-D,L-2-aminobutyrolactone, DL-N-(2,6-dimethlphenyl)N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl) pentyl]-1H-1,2,4-triazole, 2,4-difluoro-α-(1H-1,2,4-triazolyl-1-methyl)-benzhydryl alcohol, N-(3-chloro-2,6-dinitro-4-trifluoromethyl-phenyl)-5-trifluoromethyl-3-chloro-2-amino-pyridine, 1-((bis-(4-fluorophenyl)-methylsilyl)-methyl)-1H-1,2,4-triazole.

Synthesis Examples

The procedures given in the Synthesis Examples below were used to prepare further compounds I by appropriate modification of the starting materials. The compounds obtained in this manner are listed in the Tables which follow, together with physical data.

1. Preparation of methyl 2,6-dimethylphenylglyoxylate

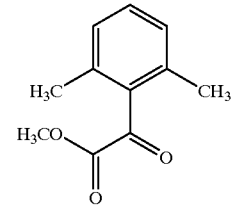

At room temperature, a Grignard solution of 18.2 g (0.76 mol) of magnesium turnings, 140 g (0.76 mol) of bromo-meta-xylene and 500 ml of tetrahydrofuran was mixed with a mixture of 109 g (0.8 mol) of zinc chloride and 500 ml of tetrahydrofuran. After about 60 min, a solution of 93 g (0.76 mol) of methyl oxalyl chloride and 250 ml of tetrahydrofuran was added dropwise at from 0° C. to –5° C. to the reaction mixture. After about 12 h at room temperature, the reaction mixture was mixed with water with ice cooling. The resulting mixture was extracted repeatedly with diethyl ether. The combined organic phases were washed with water and $NaHCO_3$ solution, dried and freed of the solvent at reduced pressure. The resulting residue was purified by distillation. This gave 48 g of the title compound as a yellowish, free-flowing liquid.

$^1$H-NMR (δ in ppm; $CDCl_3$): 2.2 (s, 6H); 3.8 (s, 3H); 7.0–7.3 (m, 3H).

2. Preparation of methyl 2,6-dimethylphenylglyoxylate O-methyloxime (E,Z mixture)

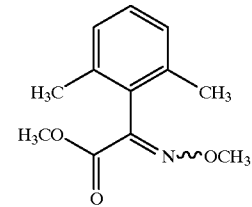

At room temperature (about 25° C.), 83.5 ml (0.15 mol) of a 15% strength solution of O-methylhydroxylamine hydrochloride in methanol were added dropwise to a mixture of 19.2 g (0.1 mol) of methyl 2,6-dimethylphenylglyoxylate and 100 ml of methanol. At the boiling point of the solvent, the resulting reaction mixture was stirred under reflux for 16 hours and then admixed with a further 24 ml of the 15% strength solution of O-methylhydroxylamine hydrochloride in methanol. After a further 32 h at the boiling point of the solvent, the solvent was removed under reduced pressure. The residue was taken up in ethyl acetate. The organic phase was washed with water, dried and freed of the solvent under reduced pressure. The resulting residue (20 g) was purified by distillation. This gave 12 g of the title compound which can be subjected to the isomerization according to Example 3 without further purification.

3. Preparation of methyl 2,6-dimethylphenylglyoxylate O-methyloxime (E isomer)

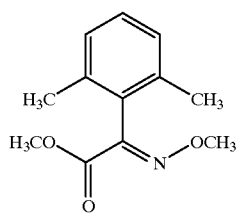

At 10° C., 65 g (0.8 mol) of HBr were introduced into a mixture of 62 g (0.28 mol) of the isomer mixture (E/Z=35/65) obtained in Example 2 and 300 ml of methylene chloride. The reaction mixture was stirred at room temperature (about 25° C.) for 60 h, and subsequently washed with water and dried. The organic solution was freed of the solvent under reduced pressure and the residue that remained was stirred with n-heptane. The solid formed in this manner was isolated and dried. This gave 32 g of the title compound. (Isomer content >90%; GC, HPLC and NMR analysis).

$^1$H-NMR (δ in ppm; CDCl$_3$): 2.1 (s, 6H); 3.8 (s, 3H); 4.0 (s, 3H); 7.0–7.3 (m, 3H).

Preparation of methyl 2-bromomethyl-6-methylphenylglyoxylate O-methyloxime (E isomer)

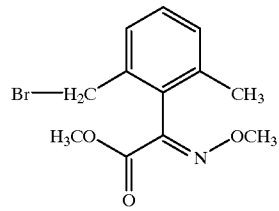

A mixture of 43.3 g (0.196 mol) of the product obtained in Example 3 and 360 ml of carbon tetrachloride was mixed with 31.4 g (0.176 mol) of N-bromosuccinimide and 0.9 g of azobisisobutyronitrile. The reaction mixture was stirred at about 80° C. for about 20 min and then cooled to room temperature (about 25° C.) and freed of solid residues. Under reduced pressure, the organic solution was freed of solvent and the residue that remained was stirred with diisopropyl ether. The solid formed in this manner was isolated, washed with diisopropyl ether/heptane (1:1) and dried. This gave 19.3 g of the title compound; mp.: 76–78° C. The filtrate was freed of solvent under reduced pressure and the resulting residue was purified by chromatography [silica gel, cyclohexane/tert-butyl methyl ether (8:1)]. This gave a further 31.6 g of the title compound.

$^1$H-NMR (δ in ppm; CDCl$_3$): 2.1 (s, 3H); 3.8 (s, 3H); 4.0 (s, 3H); 4.2 (s, 2H); 7.1–7.4 (m, 3H).

5. Preparation of methyl 2-{[(α-methyl-3-trifluoromethylbenzyl) imino]oxymethyl}-6-methylphenylglyoxylate O-methyloxime (E isomer)

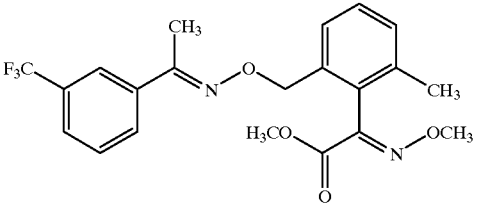

A mixture of 1.1 g (5.4 mmol) of 3-trifluoromethylacetophenone oxime and 10 ml of dimethylformamide was mixed with 1.0 g (5.4 mmol) of a 30% strength solution of sodium methoxide in methanol. After about 30 min at room temperature (about 25° C.), the reaction mixture was mixed with 1.6 g (5.9 mmol) of the compound of Example 4. After a further 30 min at room temperature (about 25° C.), the resulting reaction mixture was poured into ice-water. The mixture was extracted with tert-butyl methyl ether. The organic phases were combined, washed with water, dried and freed of the solvent under reduced pressure. The resulting residue was purified by chromatography (silica gel; cyclohexane/tert-butyl methyl ether 8:2). This gave 1.1 g of the title compound as a yellowish solid; mp.: 63–66° C.

$^1$H-NMR (δ in ppm; CDCl$_3$): 2.1 (s, 3H); 2.2 (s, 3H); 3.8 (s, 3H); 4.1 (s, 3H); 5.1 (m, 2H); 7.2–8.0 (m, 7H).

TABLE (I)

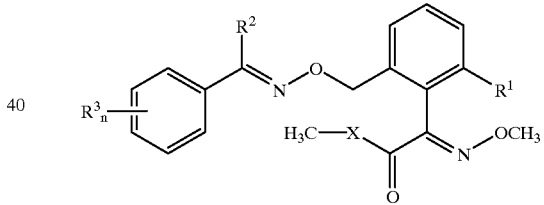

| No. | X | R$^1$ | R$^2$ | R$^3$ | Phys. data (mp[° C.], IR [cm$^{-1}$]) |
|---|---|---|---|---|---|
| I.1 | O | CH$_3$ | CH$_3$ | 3,4-Cl$_2$ | mp: 110–111 |
| I.2 | NH | CH$_3$ | CH$_3$ | 3,4-Cl$_2$ | IR: 1673, 1523, 1469, 1003, 978 |
| I.3 | O | CH$_3$ | CH$_3$ | 3-Cl | mp: 103–104 |
| I.4 | NH | CH$_3$ | CH$_3$ | 3-Cl | IR: 1672, 1524, 1038, 785 |
| I.5 | O | CH$_3$ | CH$_3$ | 4-Cl | IR: 1729, 1224, 1066, 1017 |
| I.6 | NH | CH$_3$ | CH$_3$ | 4-Cl | IR: 1671, 1524, 1038, 978 |
| I.7 | O | CH$_3$ | CH$_3$ | 3,5-Cl$_2$ | mp: 125–128 |
| I.8 | O | CH$_3$ | CH$_3$ | 3-CF$_3$ | mp: 63–66 |
| I.9 | NH | CH$_3$ | CH$_3$ | 3-CF$_3$ | IR: 1672, 1526, 1341, 1276, 1126 |
| I.10 | NH | CH$_3$ | CH$_3$ | 3-Br | IR: 1658, 1522, 1062, 1039 |
| I.11 | O | CH$_3$ | CH$_2$CH$_3$ | 4-Cl | IR: 956, 1019, 1067, 1206 |
| I.12 | NH | CH$_3$ | CH$_2$CH$_3$ | 4-Cl | mp: 94–97 |
| I.13 | O | CH$_3$ | CH$_2$CH$_3$ | 4-F | mp: 54–57 |
| I.14 | NH | CH$_3$ | CH$_2$CH$_3$ | 4-F | mp: 88–91 |
| I.15 | O | CH$_3$ | CH$_2$CH$_3$ | 3-Cl | IR: 1206, 1067, 1019, 783 |
| I.16 | NH | CH$_3$ | CH$_2$CH$_3$ | 3-Cl | IR: 1670, 1524, 1038, 783 |
| I.17 | O | CH$_3$ | CH$_2$CH$_3$ | 4-CH$_3$ | IR: 1205, 1067, 1020, 956 |
| I.18 | NH | CH$_3$ | CH$_2$CH$_3$ | 4-CH$_3$ | IR: 1669, 1463, 1037, 978 |
| I.19 | O | CH$_3$ | CH$_2$CH$_3$ | 3-F | mp: 76–78 |
| I.20 | NH | CH$_3$ | CH$_2$CH$_3$ | 3-F | IR: 1659, 1524, 1080, 1039 |
| I.21 | O | CH$_3$ | CH$_2$CH$_3$ | 3-CF$_3$ | IR: 1167, 1127, 1067, 1020 |
| I.22 | NH | CH$_3$ | CH$_2$CH$_3$ | 3-CF$_3$ | mp: 112–114 |

TABLE-continued (I)

|  |  |  |  | Phys. data |
|---|---|---|---|---|
| No. | X | $R^1$ | $R^2$ | $R^3$ | (mp[° C.], IR [cm$^{-1}$]) |
| I.23 | O | $CH_3$ | $CH_3$ | 4-$CH_3$ | IR: 1317, 1206, 1067, 1019 |
| I.24 | NH | $CH_3$ | $CH_3$ | 4-$CH_3$ | mp: 100–103 |
| I.25 | O | $CH_3$ | $CH_3$ | 4-Br | mp: 92–95 |
| I.26 | NH | $CH_3$ | $CH_3$ | 4-Br | mp: 84–87 |
| I.27 | O | $CH_3$ | $CH_3$ | $C_6H_5$ | mp: 94–96 |
| I.28 | NH | $CH_3$ | $CH_3$ | $C_6H_5$ | mp: 118–120 |
| I.29 | O | $CH_3$ | $CH_3$ | 4-$CF_3$ | mp: 91–93 |
| I.30 | NH | $CH_3$ | $CH_3$ | 4-$CF_3$ | mp: 103 . 105 |
| I.31 | O | $CH_3$ | $CH_3$ | 3-F | mp: 93–95 |
| I.32 | NH | $CH_3$ | $CH_3$ | 3-F | mp: 109–111 |
| I.33 | O | $CH_3$ | $CH_3$ | 4-F | mp: 101–104 |
| I.34 | NH | $CH_3$ | $CH_3$ | 4-F | mp: 113–115 |
| I.35 | O | $CH_3$ | $CH_3$ | 3-$CH_3$ | mp: 92–95 |
| I.36 | NH | $CH_3$ | $CH_3$ | 3-$CH_3$ | mp: 94–97 |
| I.37 | O | $CH_3$ | $CH_3$ | 3,4 $(CH_3)_2$ | mp: 112–115 |
| I.38 | NH | $CH_3$ | $CH_3$ | 3,4 $(CH_3)_2$ | mp: 132–134 |
| I.39 | O | $CH_3$ | $CH_3$ | 3-Br | mp: 90–93 |

Examples of the activity against harmful fungi

The improved fungicidal activity of the compounds of the general formula I could be demonstrated by the tests which follow. The known active compounds (A) served as comparative compounds of the prior art:

(A)

| No. | $R^3_n$ | X |
|---|---|---|
| A.1 | 3-Cl | O |
| A.2 | 4-Cl | O |
| A.3 | 3,5-$Cl_2$ | O |
| A.4 | 3,4-$Cl_2$ | O |
| A.5 | 3-Cl | NH |
| A.6 | 4-Cl | NH |

The active compounds were prepared as a 10% strength emulsion in a mixture of 63% by weight of cyclohexanone and 27% by weight of emulsifier and diluted with water to the desired concentration.

Use Example 1
Activity against *Botrytis cinerea* in bell peppers

Bell pepper seedlings cv. "Neusiedler Ideal Elite" having 4–5 well developed leaves were sprayed to run off point with an aqueous active compound preparation (application rate: 250 ppm). The next day, the treated plants were inoculated with a spore suspension of *Botrytis cinerea* containing 1.7×10$^6$ spores/ml in a 2% strength aqueous biomalt solution. The test plants were subsequently placed in a climatized chamber at 22 to 24° C. and high atmospheric humidity. After 5 days, the extent of the fungal infection of the leaves could be determined visually in %.

| Active compound No. | Fungal infection [%] |
|---|---|
| I.3 | 5 |
| A.1 | 60 |
| I.5 | 15 |
| A.2 | 80 |
| I.7 | 15 |
| A.3 | 60 |
| untreated | 80 |

Use Example 2
Curative activity against *Plasmopara viticola*

Leaves of potted vines cv. "Müller-Thurgau" were inoculated with an aqueous zoospore suspension of *Plasmopara viticola*. The vines were subsequently kept at 22–24° C. in a chamber saturated with water vapor for 48 hours. They were then removed from the chambers and, after drying, sprayed with an aqueous preparation of active compound (application rate: 63 ppm) to run off point. After the spray coating had dried on, the plants were further cultivated in a greenhouse at from 20 to 30° C. for 5 days. After this time, the plants were once more placed in a humid climatized chamber for 16 hours to promote the eruption of sporangiophores. The extent of fungal infection on the underside of the leaves was then determined visually.

| Active compound No. | Fungal infection [%] |
|---|---|
| I.1 | 25 |
| A.4 | 40 |
| I.4 | 15 |
| A.5 | 40 |
| untreated | 80 |
| I.6 | 25 |
| A.6 | 80 |
| untreated | 80 |

In a corresponding test, plants which had been treated with the compound I.6 showed an infection of 5%.

Examples of the activity against animal pests

The active compounds were prepared a. as a 0.1% strength solution in acetone or b. as a 10% strength emulsion in a mixture of 70% by weight of cyclohexanone, 20% by weight of Nekanil® LN (Lutensol® AP6, wetting agent having an emulsifying and dispersing action and based on ethoxylated alkylphenols) and 10% by weight of Wettol® EM (nonionic emulsifier based on ethoxylated castor oil)

and were diluted to the desired concentration with acetone in the case of a. or with water in the case of b.

After the end of the experiments, the lowest concentration, in each case, at which the compounds still showed an 80 to 100% inhibition or kill rate (activity threshold or minimum concentration) in comparison with untreated control experiments was determined.

We claim:

1. A phenylketiminooxybenzyl compound of formula I

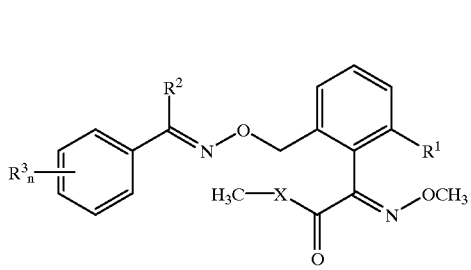

(I)

wherein

X is O or NH;

$R^1$ is fluorine, chlorine, $C_1$–$C_4$-alkyl, $C_1$–$C_4$-haloalkyl, $C_1$–$C_4$-alkoxy and $C_1$–$C_4$-haloalkoxy;

$R^2$ is halogen, $C_1$–$C_4$-alkyl, $C_1$–$C_4$-haloalkyl and $C_1$–$C_4$-alkoxy;

$R^3$ is halogen, $C_1$–$C_4$-alkyl, $C_1$–$C_4$-haloalkyl, $C_1$–$C_4$-alkoxy, $C_1$–$C_4$-haloalkoxy, $C_3$–$C_6$-cycloalkyl, phenyl or phenoxy, wherein the phenyl radicals are unsubstituted or carry one to three of the following groups: halogen, $C_1$–$C_4$-alkyl, $C_1$–$C_4$-haloalkyl, $C_1$–$C_4$-alkoxy and $C_1$–$C_4$-haloalkoxy;

$CR^a$=$NOR^b$, wherein $R^a$ is hydrogen or $C_1$–$C_4$-alkyl and $R^b$ is $C_1$–$C_4$-alkyl, $C_3$–$C_4$-alkenyl or $C_3$–$C_4$-alkynyl;

n is 1, 2 or 3, wherein the radicals $R^3$ are identical or different when n is 2 or 3, and salts thereof.

2. A process for preparing the compound of formula I defined in claim 1, which comprises reacting an N-hydroxyketimine of formula IIa

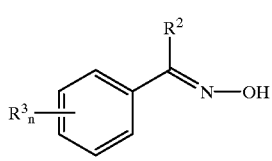

(IIa)

in an inert solvent with a benzyl compound of formula IIIa

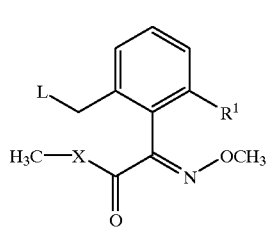

(IIIa)

wherein L is a leaving group.

3. A process for preparing the compound of formula I defined in claim 1, which comprises reacting a phenyl ketone of formula IIb

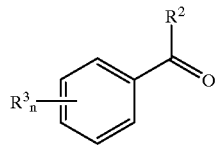

(IIb)

in an inert solvent with an O-benzylhydroxylamine of formula IIIb.

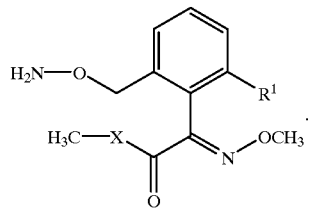

(IIIb)

4. A composition suitable for controlling animal pests or harmful fungi comprising a solid or liquid carrier and the compound of formula I defined in claim 1.

5. A method for controlling harmful fungi, which comprises treating the fungi or materials, plants, soil or seeds to be protected from being attacked by the fungi with an effective amount of the compound of formula I defined in claim 1.

6. A method for controlling animal pests, which comprises treating the pests or rooms, materials, plants, soil or seeds to be protected from the pests with an effective amount of the compound of formula I defined in claim 1.

7. The compound of formula I defined in claim 1, wherein X is oxygen.

8. The compound of formula I defined in claim 1, wherein X is NH.

9. The compound of formula I defined in claim 1, wherein $R^1$ is fluorine, chlorine, $C_1$–$C_2$-alkyl, $C_1$–$C_2$-haloalkyl, $C_1$–$C_2$-alkoxy or $C_1$–$C_2$-haloalkoxy.

10. The compound of formula I defined in claim 1, wherein $R^1$ is fluorine, chlorine, methyl, trifluoromethyl, methoxy, difluoromethoxy or trifluoromethoxy.

11. The compound of formula I defined in claim 1, wherein $R^2$ is fluorine, chlorine, bromine, $C_1$–$C_2$-alkyl, $C_1$–$C_2$-haloalkyl and $C_1$–$C_4$-alkoxy.

12. The compound of formula I defined in claim 1, wherein $R^2$ is chlorine, methyl, trifluoromethyl, methoxy, ethoxy or isopropyloxy.

13. The compound of formula I defined in claim 1, wherein a group $R^3$ is bonded to the 3 or the 4 position of the phenyl ring.

14. The compound of formula I defined in claim 1, wherein one group $R^3$ is bonded to the 3 position of the phenyl ring and one group $R^3$ is bonded to the 4 or 5 position of the phenyl ring.

15. The compound of formula I defined in claim 1, wherein groups $R^3$ are bonded to the 2, 4 and 5 position of the phenyl ring.

16. The compound of formula I defined in claim 1, wherein $R^3$ is selected from the group consisting of one to three of halogen, $C_1$–$C_2$-alkyl, $C_1$–$C_2$-haloalkyl, $C_1$–$C_3$-alkoxy, $C_1$–$C_2$-haloalkoxy and $C_3$–$C_6$-cycloalkyl, and one of phenyl and phenoxy, wherein the phenyl radicals are unsubstituted or carry one to three of the following groups: halogen, $C_1$–$C_2$-alkyl, $C_1$–$C_2$-haloalkyl, $C_1$–$C_3$-alkoxy and $C_1$–$C_2$-haloalkoxy, and one of $CR^a$=$NOR^b$, wherein $R^a$ is hydrogen or $C_1$–$C_4$-alkyl, and $R^b$ is $C_1$–$C_4$-alkyl, $C_3$–$C_4$-alkenyl or $C_3$–$C_4$-alkynyl.

17. The compound of formula I defined in claim 1, wherein $R^3$ is selected from the group consisting of one to three of fluorine, chlorine, methyl, difluoromethyl, trifluoromethyl, methoxy, isopropyloxy, difluoromethoxy, trifluoromethoxy and cyclopropyl, and one of phenyl and phenoxy, wherein the phenyl radicals are unsubstituted or carry one to three of the following groups: fluorine, chlorine, methyl, difluoromethyl, trifluoromethyl, methoxy, isopropyloxy, difluoromethoxy and trifluoromethoxy, and one of $CR^a$=$NOR^b$, where $R^a$ is hydrogen or methyl, and $R^b$ is methyl, ethyl, isopropyl, allyl, 2-butenyl, propargyl or 2-butynyl.

18. The compound of formula I defined in claim 1, wherein $R^1$ is fluorine, chlorine, methyl, trifluoromethyl, methoxy or trifluoromethoxy;

$R^2$ is fluorine, chlorine, methyl, trifluoromethyl or methoxy;

$R^3$ is fluorine, chlorine, methyl, trifluoromethyl, methoxy, trifluoromethoxy, cyclopropyl, phenyl or phenoxy, wherein the phenyl radicals are unsubstituted or carry one to three of the following groups: fluorine, chlorine, methyl, trifluoromethyl, methoxy and trifluoromethoxy;

CH=NOCH$_3$, CH=NOCH$_2$CH$_3$, CH=NOCH$_2$CH$_2$CH$_3$, CH=NOCH(CH$_3$)$_2$, CH=NOCH$_2$CH=CH$_2$, CH=NOCH$_2$CH=CHCH$_3$, CH=NOCH$_2$C≡CH, CH=NOCH$_2$C≡CCH$_3$, C(CH$_3$)=NOCH$_3$, C(CH$_3$)=NOCH$_2$CH$_3$, C(CH$_3$)=NOCH$_2$CH$_2$CH$_3$, C(CH$_3$)=NOCH(CH$_3$)$_2$, C(CH$_3$)=NOCH$_2$CH=CH$_2$, C(CH$_3$)=NOCH$_2$CH=CHCH$_3$, C(CH$_3$)=NOCH$_2$C≡CH and C(CH$_3$)=NOCH$_2$C≡CCH$_3$.

* * * * *

UNITED STATES PATENT AND TRADEMARK OFFICE
CERTIFICATE OF CORRECTION

PATENT NO. : 6,187,816 B1  
DATED : February 13, 2001  
INVENTOR(S) : Grammenos et al.

Page 1 of 1

It is certified that error appears in the above-identified patent and that said Letters Patent is hereby corrected as shown below:

<u>Column 36, claim 18,</u>  
Line 16, should read:  
-- CH=NOCH$_2$C≡CH, CH=NOCH$_2$C≡CCH$_3$, --.  
Lines 20-21, should read:  
-- CH=CHCH$_3$, C(CH$_3$)=NOCH$_2$C≡CH and C(CH$_3$)=NOCH$_2$C≡CCH$_3$. --

Signed and Sealed this

Sixth Day of November, 2001

Attest:

NICHOLAS P. GODICI  
Attesting Officer    *Acting Director of the United States Patent and Trademark Office*